US008917078B2

(12) United States Patent
Kondo et al.

(10) Patent No.: US 8,917,078 B2
(45) Date of Patent: Dec. 23, 2014

(54) FREQUENCY MEASURING DEVICE AND ODOR SENSOR AND ELECTRONIC EQUIPMENT WHICH ARE PROVIDED WITH THE FREQUENCY MEASURING DEVICE

(75) Inventors: Takayuki Kondo, Chino (JP); Masayoshi Todorokihara, Munich (DE)

(73) Assignee: Seiko Epson Corporation, Tokyo (JP)

( * ) Notice: Subject to any disclaimer, the term of this patent is extended or adjusted under 35 U.S.C. 154(b) by 515 days.

(21) Appl. No.: 13/158,775

(22) Filed: Jun. 13, 2011

(65) Prior Publication Data

US 2011/0309821 A1 Dec. 22, 2011

(30) Foreign Application Priority Data

Jun. 16, 2010 (JP) .................................. 2010-137267

(51) Int. Cl.
*G01R 23/00* (2006.01)
*G01N 29/02* (2006.01)

(52) U.S. Cl.
CPC ................................... *G01N 29/022* (2013.01)
USPC ...................................................... 324/76.49

(58) Field of Classification Search
None
See application file for complete search history.

(56) References Cited

U.S. PATENT DOCUMENTS

| 5,005,413 | A | * | 4/1991 | Novack et al. ............. 73/514.29 |
| 5,231,880 | A | * | 8/1993 | Ward et al. ...................... 73/702 |
| 5,379,639 | A | * | 1/1995 | Hulsing et al. ............ 73/514.29 |
| 5,447,869 | A | | 9/1995 | Okahata |
| 5,546,810 | A | * | 8/1996 | Arikawa et al. ................. 73/702 |
| 6,230,565 | B1 | * | 5/2001 | Foote .......................... 73/514.29 |
| 6,806,698 | B2 | * | 10/2004 | Gauthier et al. ........... 324/76.41 |
| 7,387,435 | B2 | * | 6/2008 | Kishi ............................ 374/117 |
| 7,659,654 | B2 | * | 2/2010 | Kondo ......................... 310/330 |
| 7,803,632 | B2 | * | 9/2010 | Okaguchi et al. ............ 436/150 |
| 8,247,948 | B2 | * | 8/2012 | Kondo .......................... 310/333 |
| 8,390,385 | B2 | * | 3/2013 | Kondo ............................ 331/46 |
| 2010/0095774 | A1 | | 4/2010 | Sone et al. |

FOREIGN PATENT DOCUMENTS

| JP | A- 63-222248 | 9/1988 |
| JP | A-1-244335 | 9/1989 |
| JP | 06-013983 | 1/1994 |
| JP | A-10-142134 | 5/1998 |
| WO | WO 2008069247 A1 | 6/2008 |

* cited by examiner

*Primary Examiner* — Paresh Patel
(74) *Attorney, Agent, or Firm* — Oliff PLC (57) ABSTRACT

A frequency measuring device according to an embodiment of the invention includes a first resonator provided with a first adsorption film, a second resonator provided with a second adsorption film, a first oscillation circuit which is connected to the first resonator and is provided with a first frequency regulator that can regulate the frequency of a first oscillation signal and output the first oscillation signal, a second oscillation circuit which is connected to the second resonator and is provided with a second frequency regulator that can regulate the frequency of a second oscillation signal and output the second oscillation signal, a measuring circuit which can measure the frequencies of the first oscillation signal and the second oscillation signal, and a control circuit which can control the first frequency regulator and the second frequency regulator.

12 Claims, 8 Drawing Sheets

FREQUENCY MEASURING DEVICE AND ODOR SENSOR AND ELECTRONIC EQUIPMENT WHICH ARE PROVIDED WITH THE FREQUENCY MEASURING DEVICE

The entire disclosure of Japanese Patent Application No. 2010-137267, filed Jun. 16, 2010 is expressly incorporated by reference herein.

BACKGROUND

1. Technical Field

An embodiment of the present invention relates to a frequency measuring device etc. provided with a plurality of sets of a resonator having an adsorption film and an oscillation circuit connected to the resonator.

2. Related Art

A phenomenon occurs in which, when a substance contained in a surrounding medium is attached to the surface of a quartz crystal resonator under a resonant condition, the resonance frequency changes according to the attached substance. A technique using this phenomenon is called QCM (quartz crystal microbalance) and used as a sensor detecting the presence and the amount of molecules contained in the surrounding medium. As the application of QCM, there is an odor sensor having a resonator with a surface on which an adsorption film which selectively adsorbs a particular molecule is formed. Moreover, the application of QCM to a biosensor, a gas sensor, etc. using DNA hybridization has also been studied. Hereinafter, descriptions will be given by taking up mainly the odor sensor as an example.

In general, an AT cut quartz crystal resonator is used in a QCM device. AT cut refers to a cut substrate having a particular orientation with respect to a quartz crystal axis, and is widely used, not only in the QCM device, because AT cut has a temperature coefficient whose change becomes minimum at temperatures near ambient temperature and thereby has high temperature stability.

The AT cut quartz crystal resonator operates in so-called thickness-shear vibration mode in which the front surface and the back surface slide alternately when a voltage is applied between the excitation electrodes formed on the front and back of the substrate. The resonance frequency $f_0$ thereof is inversely proportional to the quartz crystal board thickness of an area sandwiched between the front and back electrodes, and the following relationship generally holds.

$$f_0(\text{MHz}) = 1670/\text{quartz crystal board thickness (μm)}$$

In addition, it is known that the relationship between the amount $\Delta M$ of adsorbed substance and the magnitude $\Delta f$ of the frequency change of the QCM device using the AT cut quartz crystal resonator is expressed by the following Sauerbrey equation:

$$\Delta f = -\frac{2 \times f_0^2}{\sqrt{\rho \times \mu}} \times \frac{\Delta M}{A}$$

wherein $f_0$ is the resonance frequency of the resonator, $\rho$ is the density of quartz crystal, $\mu$ is the shear modulus of quartz crystal, and A is the effective oscillating area (which is nearly equal to the electrode area). As is clear from the equation above, by increasing the resonance frequency $f_0$ of the quartz crystal resonator, it is possible to increase the sensitivity, that is, the magnitude $\Delta f$ of the frequency change per amount $\Delta M$ of adsorbed substance.

Incidentally, an odor sensor using a QCM device has been disclosed in JP-A-63-222248 (Patent Document 1), for example. In the technique disclosed in Example 6 of Patent Document 1, the presence of an odorous substance β-ionone with which the air is saturated is detected as a change in the frequency (FIG. 9) by using an element (FIG. 6) provided with an AT cut quartz crystal resonator 1 having an electrode 2 on which a bilayer membrane film formed of dialkylammonium salt and polystyrene sulfonic acid is formed as an adsorption film.

However, in reality, it is impossible to make the adsorption film selectively adsorb only a target substance, and a plurality of substances are adsorbed onto the adsorption film. To solve this problem, in the technique disclosed in JP-A-1-244335 (Patent Document 2), for example, a so-called multiarray method is adopted by which the type of odor is identified by concurrently observing the changes in the frequencies of a plurality of quartz crystal resonators on which different types of adsorption films are formed and performing pattern analysis of the ratio between the changes in the frequencies of the resonators.

Here, to improve the accuracy of identification of odors, increasing the types of resonators used, the resonators provided with the adsorption films, is effective. However, 400,000 types of odorous substances to be measured are considered to exist, and it is impossible to identify such an enormous number of types of odorous substances by using several (several types of) resonators (QCM) as in the existing techniques described above.

When a large number of resonators (QCM) are used as described above, a drawing effect between the oscillation circuits connected to the resonators sometimes becomes a problem. The drawing effect here refers to a phenomenon in which, when the oscillation frequencies of two oscillation circuits are close to each other, something triggers a change by which one of the frequencies of the signals output from these oscillation circuits suddenly coincides with the other. When the drawing effect occurs, the frequency of the signal output from the oscillation circuit changes irrespective of the substance attached to the adsorption film.

In JP-A-10-142134 (Patent Document 3), to prevent the drawing effect, a plurality of sorted resonators having different resonance frequencies are used.

However, even when the resonators having different resonance frequencies are sorted and used as described in Patent Document 3, the characteristics such as load capacitance included in the oscillation circuit may vary. In this case, the frequency of the signal output from the oscillation circuit may not become an intended frequency, making it impossible to obtain a desired frequency difference between the oscillation circuits. This may also cause the drawing effect.

Furthermore, when a large number of resonators are used, the resonators have to have different resonance frequencies. As a result, it takes time to perform sorting.

SUMMARY

A frequency measuring device according to an aspect of the invention includes: a first resonator provided with a first adsorption film; a second resonator provided with a second adsorption film; a first oscillation circuit which is connected to the first resonator and is provided with a first frequency regulator that can regulate the frequency of a first oscillation signal and output the first oscillation signal; a second oscillation circuit which is connected to the second resonator and is provided with a second frequency regulator that can regulate the frequency of a second oscillation signal and output the second oscillation signal; a measuring circuit which can measure the frequencies of the first oscillation signal and the second oscillation signal; and a control circuit which can control the first frequency regulator and the second frequency regulator so that a frequency difference between the first oscillation signal and the second oscillation signal becomes greater than a predetermined frequency difference based on the results of measurement performed by the measuring circuit.

According to this configuration, since the frequency difference between the first oscillation signal and the second oscillation signal which are output from the first oscillation circuit and the second oscillation circuit, respectively, is made greater than the predetermined frequency difference, it is possible to prevent the drawing effect from occurring between the oscillation circuits. This eventually makes it possible to prevent the drawing effect from causing a problem in the operation of the frequency measuring device.

Moreover, this eliminates the need to sort out resonators having a predetermined resonance frequency in advance. In addition, since there is no need to sort out such resonators, there is no surplus of resonators having a certain resonance frequency. This also makes it possible to enhance yield.

Furthermore, the frequency measuring device according to the aspect of the invention may include: a third resonator provided with a third adsorption film; and a third oscillation circuit which is connected to the third resonator and is provided with a third frequency regulator that can regulate the frequency of a third oscillation signal and output the third oscillation signal, wherein the measuring circuit can further measure the frequency of the third oscillation signal, and the control circuit can perform the processes of (a1) specifying a signal having the highest frequency, the signal of the first oscillation signal, the second oscillation signal, and the third oscillation signal, as a first signal and specifying a signal having the second highest frequency after the first signal as a second signal based on the frequencies measured by the measuring circuit, (b) comparing the first signal and the second signal, (c1-1) specifying the second signal as a new first signal when a frequency difference between the first signal and the second signal is greater than a predetermined frequency difference, specifying a signal having the second highest frequency after the new first signal as a new second signal, and returning to the process (b), and (c1-2) decreasing the frequency of the second signal by controlling the frequency regulator corresponding to the oscillation circuit outputting the second signal when the frequency difference between the first signal and the second signal is smaller than or equal to the predetermined frequency difference and returning to the process (a1).

According to this configuration, since the frequency difference between the first to third oscillation signals is made greater than the predetermined frequency difference, it is possible to prevent the drawing effect from occurring between these oscillation circuits. Moreover, by using the control circuit configured as described above, it is possible to make the frequency difference between the oscillation signals greater than the predetermined frequency difference easily and appropriately.

Furthermore, in the control circuit configured as described above, the frequency is decreased when the frequencies of the oscillation signals are regulated. This makes it possible to regulate the frequencies of the oscillation signals without increasing the power consumption of the frequency measuring device.

In addition, the frequency measuring device according to another aspect of the invention may include: a third resonator provided with a third adsorption film; and a third oscillation circuit which is connected to the third resonator and can output a third oscillation signal having a frequency which can be regulated by a third frequency regulator, wherein the measuring circuit can further measure the frequency of the third oscillation signal, and the control circuit can perform the processes of (a2) specifying a signal having the lowest frequency, the signal of the first oscillation signal, the second oscillation signal, and the third oscillation signal, as a first signal and specifying a signal having the second lowest frequency after the first signal as a second signal based on the frequencies measured by the measuring circuit, (b) comparing the first signal and the second signal, (c2-1) specifying the second signal as a new first signal when a frequency difference between the first signal and the second signal is greater than a predetermined frequency difference, specifying a signal having the second lowest frequency after the new first signal as a new second signal, and returning to the process (b), and (c2-2) increasing the frequency of the second signal by controlling the frequency regulator corresponding to the oscillation circuit outputting the second signal when the frequency difference between the first signal and the second signal is smaller than or equal to the predetermined frequency difference and returning to the process (a1).

According to this configuration, as is the case with the configuration described earlier, since the frequency difference between the first to third oscillation signals is made greater than the predetermined frequency difference, it is possible to prevent the drawing effect from occurring between these oscillation circuits. Moreover, by using the control circuit configured as described above, it is possible to make the frequency difference between the oscillation signals greater than the predetermined frequency difference easily and appropriately.

Furthermore, the frequency measuring device according to the aspect of the invention may include: a third resonator provided with a third adsorption film; and a third oscillation circuit which is connected to the third resonator and can output a third oscillation signal having a frequency which can be regulated by a third frequency regulator, wherein the measuring circuit can further measure the frequency of the third oscillation signal, and the control circuit can perform the processes of (a1) specifying a signal having the highest frequency, the signal of the first oscillation signal, the second oscillation signal, and the third oscillation signal, as a first signal and specifying a signal having the second highest frequency after the first signal as a second signal based on the frequencies measured by the measuring circuit, (b) comparing the first signal and the second signal, (c1-1) specifying the second signal as a new first signal when a frequency difference between the first signal and the second signal is greater than a predetermined frequency difference, specifying a signal having the second highest frequency after the new first signal as a new second signal, and returning to the process (b), and (c3-2) decreasing the frequency of the second signal by controlling the frequency regulator corresponding to the oscillation circuit outputting the second signal when the frequency difference between the first signal and the second signal is smaller than or equal to the predetermined frequency difference, specifying a signal having the second highest frequency after the first signal, the signal of the first oscillation signal, the second oscillation signal, and the third oscillation signal, as a new second signal, and returning to the process (b).

According to this configuration, it is possible to make the frequency difference between the first to third oscillation signals greater than the predetermined frequency difference in a shorter time while making adjustments to decrease the frequency of the oscillation signal.

In addition, the frequency measuring device according to the aspect of the invention may include: a third resonator provided with a third adsorption film; and a third oscillation circuit which is connected to the third resonator and can output a third oscillation signal having a frequency which can be regulated by a third frequency regulator, wherein the measuring circuit can further measure the frequency of the third oscillation signal, and the control circuit can perform the processes of (a2) specifying a signal having the lowest frequency, the signal of the first oscillation signal, the second oscillation signal, and the third oscillation signal, as a first signal and specifying a signal having the second lowest frequency after the first signal as a second signal based on the frequencies measured by the measuring circuit, (b) comparing the first signal and the second signal, (c2-1) specifying the second signal as a new first signal when a frequency difference between the first signal and the second signal is greater than a predetermined frequency difference, specifying a signal having the second lowest frequency after the new first signal as a new second signal, and returning to the process (b), and (c4-2) increasing the frequency of the second signal by controlling the frequency regulator corresponding to the oscillation circuit outputting the second signal when the frequency difference between the first signal and the second signal is smaller than or equal to the predetermined frequency difference, specifying a signal having the second lowest frequency after the first signal, the signal of the first oscillation signal, the second oscillation signal, and the third oscillation signal, as a new second signal, and returning to the process (b).

According to this configuration, it is possible to make the frequency difference between the first to third oscillation signals greater than the predetermined frequency difference in a shorter time while making adjustments to increase the frequency of the oscillation signal.

Moreover, the control circuit may end the processes when determining that a frequency difference between the first oscillation signal, the second oscillation signal, and the third oscillation signal becomes greater than a predetermined frequency difference.

Furthermore, the first oscillation circuit and the second oscillation circuit each may have a resistance element connected between a first terminal and a second terminal of the resonator, an inverter connected between the first terminal and the second terminal in parallel with the resistance element, a variable capacitance element connected between the first terminal and a first potential terminal, and a first capacitative element connected between the second terminal and the first potential terminal.

According to this configuration, it is possible to provide a frequency measuring device provided with an oscillation circuit with a relatively simple configuration.

In addition, the first frequency regulator and the second frequency regulator each may include a voltage regulating circuit which can change a voltage to be applied to the variable capacitance element.

According to this configuration, it is possible to provide a frequency measuring device which can regulate the frequencies of the oscillation signals easily by changing the applied voltage.

Moreover, the voltage regulating circuit may include an analog filter circuit.

According to this configuration, it is possible to provide a frequency measuring device provided with a voltage regulating circuit with a simple configuration using an analog device.

Furthermore, the first frequency regulator and the second frequency regulator each may include a drive voltage regulating circuit which can change a drive voltage of the corresponding first oscillation circuit or second oscillation circuit.

According to this configuration, it is possible to provide a frequency measuring device which can regulate the frequencies of the oscillation signals only by changing the drive voltage.

In addition, a serial-parallel converter generating a first selection signal and a second selection signal based on a 1-bit control signal supplied from the outside may be further provided, the drive voltage regulating circuit may further include a first drive voltage regulating resistance element and a first switching element which are connected in series between a terminal of the drive voltage and a second potential terminal and a second drive voltage regulating resistance element and a second switching element which are connected in series between the terminal of the drive voltage and the second potential terminal and connected in parallel with the first drive voltage regulating resistance element, and a conducting state of the first switching element may be changed by the first selection signal and a conducting state of the second switching element may be changed by the second selection signal.

According to this configuration, it is possible to control a plurality of switching elements of the drive voltage regulating circuit by a 1-bit control signal. This makes it possible to reduce the number of signal lines used and facilitate connection between the control circuit and the oscillation circuit.

Another aspect of the invention is directed to an odor sensor provided with any one of the frequency measuring devices described above.

Still another aspect of the invention is directed to electronic equipment provided with the frequency measuring device described above.

BRIEF DESCRIPTION OF THE DRAWINGS

The invention will be described with reference to the accompanying drawings, wherein like numbers reference like elements.

DESCRIPTION OF EXEMPLARY EMBODIMENTS

Embodiments of the invention will be described specifically with reference to the drawings according to the composition below. It is to be understood that the embodiments of the invention described below are mere examples of the invention and are not meant to limit the technical scope of the invention. Incidentally, in the drawings, the same parts will be identified with the same reference numerals, and their explanations are sometimes omitted.

1. Definition
2. First embodiment
    (1) Configuration example of frequency measuring device
    (2) Configuration example of oscillation circuit
    (3) Configuration example of controlled potential regulating circuit
    (4) Example of operation of frequency measuring device
    (5) Feature of first embodiment
3. Second embodiment
    (1) Configuration example of drive voltage generating circuit
    (2) Feature of second embodiment
4. Third embodiment
    (1) Example of operation of frequency measuring device
    (2) Feature of third embodiment
5. Supplement

1. DEFINITION

First, a term used in this specification is defined as follows.

An "XX circuit" (XX is an arbitrary word) includes a circuit formed as an electrical circuit, but is not limited thereto: it also includes physical means serving as the circuit or functional means implemented via software. Moreover, the function of one circuit may be implemented by two or more physical or functional means, or the functions of two or more circuits may be implemented by one physical or functional means.

2. FIRST EMBODIMENT

The configuration and operation of a frequency measuring device in a first embodiment of the invention will be described with reference to FIGS. 1 to 5.

Incidentally, the frequency measuring device described in the embodiments including the first embodiment is used in an instrument such as an odor sensor identifying the odor of a surrounding medium, for example, based on the frequency measured by a counter circuit or a control circuit. In the odor sensor, in addition to the frequency measuring device which will be described in the embodiments, a database for identification of odors is prepared, and the odor sensor can identify the odor by referring to the data stored in the database based on a change in the frequency measured by the frequency measuring device and output from each oscillation circuit. Hereinafter, the frequency measuring device, which is a characteristic part of the present invention, will be described, and the instrument such as the odor sensor will not be described specifically.

(1) Configuration Example of Frequency Measuring Device

Figure 1:
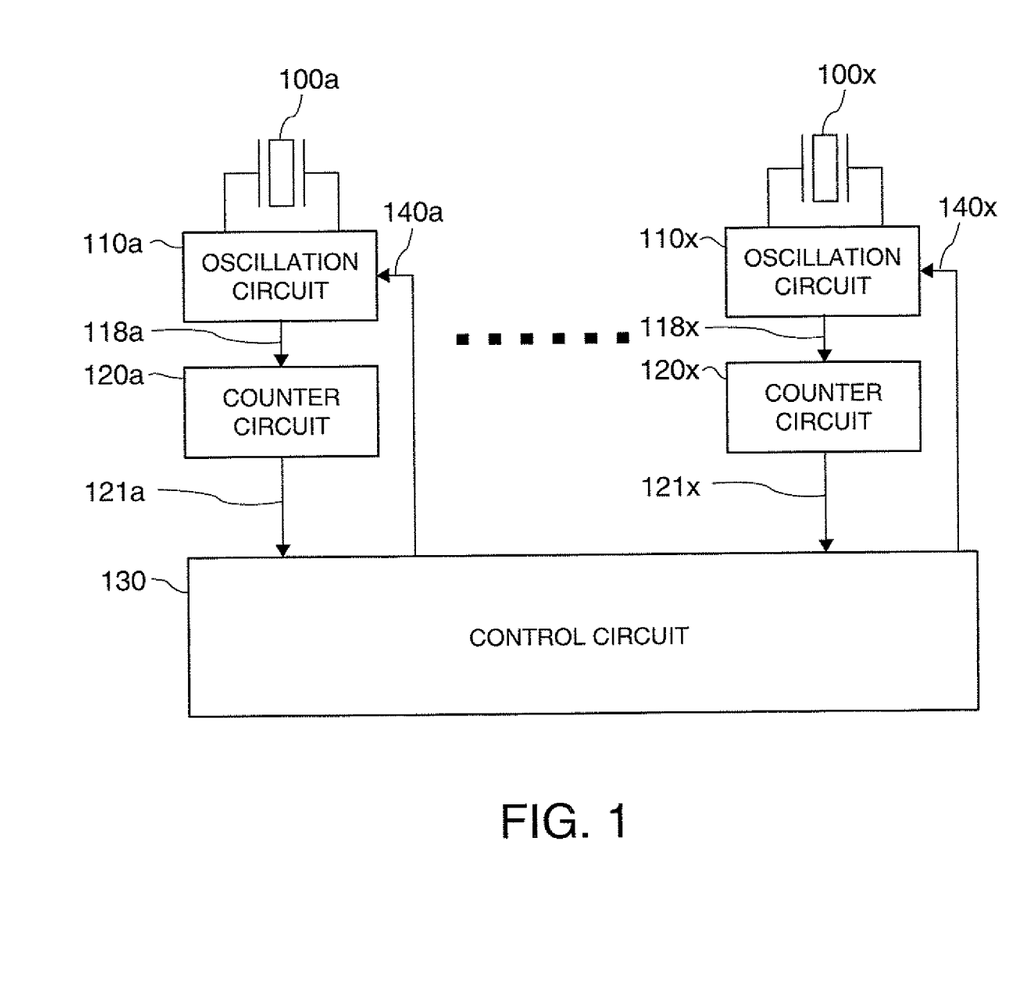
FIG. 1 is a diagram showing a configuration example of a frequency measuring device.

FIG. 1 is a diagram showing the configuration of the frequency measuring device in the first embodiment. As shown in FIG. 1, the frequency measuring device includes quartz crystal resonators $100a$ to $100x$, oscillation circuits $110a$ to $110x$, counter circuits $120a$ to $120x$, and a control circuit $130$. That is, the frequency measuring device includes a plurality of sets (n sets) of configurations each being formed of a quartz crystal resonator $100$, an oscillation circuit $110$, and a counter circuit $120$, and includes one control circuit $130$ connected to the plurality of counter circuits $120$ in these configurations.

Quartz Crystal Resonators $100a$ to $100x$

Each of the quartz crystal resonators $100a$ to $100x$ has front and back surfaces on which an electrode pair is formed and is connected to a corresponding one of the oscillation circuits $110a$ to $110x$ via the electrode pair. The quartz crystal resonators $100a$ to $100x$ each operate in so-called thickness-shear vibration mode in which the front surface and the back surface slide alternately when a voltage is applied to the electrode pair. Moreover, the quartz crystal resonators $100a$ to $100x$ are provided on the same substrate.

On the surface of the electrode of each of the quartz crystal resonators $100a$ to $100x$, an adsorption film having the property of adsorbing a particular substance is provided. The surrounding medium of the quartz crystal resonators $100a$ to $100x$ is mainly gas, but may be liquid or a mixture of gas and liquid. The adsorption films used in the quartz crystal resonators differ from quartz crystal resonator to quartz crystal resonator, and, in this embodiment, the quartz crystal resonators $100a$ to $100x$ are provided with different adsorption films. The adsorption film is formed on one side or both sides of each of the quartz crystal resonators $100a$ to $100x$; however, it is preferable that the adsorption film be formed on both sides thereof. When the adsorption film is formed on both sides, it is possible to adsorb a substance to be adsorbed more effectively than when the adsorption film is formed on one side. Incidentally, as the adsorption film, any one of a polymeric film, a lipid film, a protein film, and a monomolecular film is used. Moreover, it is preferable that different types of adsorption films easily adsorb different types of molecules.

Incidentally, in the above configuration, all the quartz crystal resonators $100a$ to $100x$ are provided with the adsorption film. Instead, one of the quartz crystal resonators $100a$ to $100x$ may be provided with no adsorption film. In this case, since the frequency of an oscillation signal output from the oscillation circuit $110a$ connected to the quartz crystal resonator $100a$ provided with no adsorption film does not change according to the substance attached to the adsorption film, this oscillation signal can be used as a signal having a reference frequency.

Oscillation Circuits $110a$ to $110x$

The oscillation circuits $110a$ to $110x$ are arranged so as to be connected to the quartz crystal resonators $100a$ to $100x$, respectively. The oscillation circuits $110a$ to $110x$ are so configured as to be able to output the oscillation signals $118a$ to $118x$, respectively. Moreover, the oscillation circuits $110a$ to $110x$ each have a frequency regulator, and these frequency regulators can regulate the frequencies of the oscillation signals $118a$ to $118x$. The specific configuration and function of the oscillation circuits $110a$ to $110x$ will be described later.

Counter Circuits $120a$ to $120x$

The counter circuits $120a$ to $120x$ are arranged so as to be connected to the oscillation circuits $110a$ to $110x$, respectively. The counter circuits $120a$ to $120x$ count the number of changes in the oscillation signals $118a$ to $118x$, respectively, which have been input from the corresponding oscillation circuits $110a$ to $110x$, and output the results of counting to the control circuit $130$ at regular time intervals. The counter circuits $120a$ to $120x$ usually count the number of occurrences of rising or falling edges of the oscillation signals $118a$ to $118x$, but the counting performed by the oscillation signals $118a$ to $118x$ is not limited thereto.

Incidentally, in the first embodiment, the counter circuits $120a$ to $120x$ corresponding to the oscillation circuits $110a$ to $110x$ are provided; however, the counter circuits $120a$ to $120x$ may be provided as one circuit.

Control Circuit 130

The control circuit 130 derives the frequencies of the oscillation signals 118a to 118x output from the oscillation circuits 110a to 110x, respectively, by performing a computation based on the results of counting input from the counter circuits 120a to 120x. Furthermore, based on the derived frequencies of the oscillation signals 118a to 118x, the control circuit 130 outputs control signals 140a to 140x for controlling the frequency regulators included in the oscillation circuits 110a to 110x in such a way that a frequency difference between the oscillation signals 118a to 118x becomes greater than a predetermined frequency difference. A specific method of control performed by the control circuit 130 will be described later.

(2) Configuration Example of Oscillation Circuit

Figure 2:
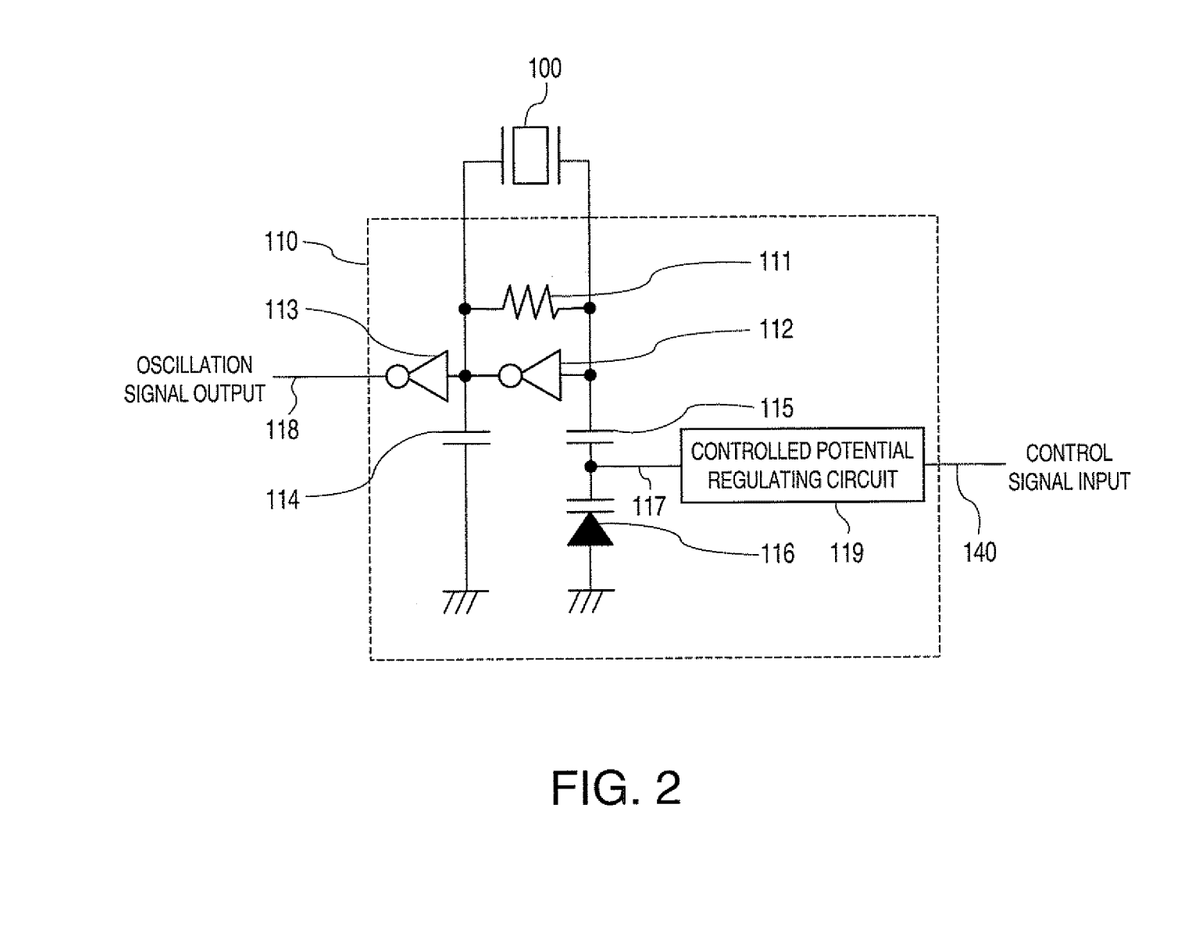
FIG. 2 is a diagram showing a configuration example of an oscillation circuit.

FIG. 2 is a diagram showing a configuration example of the oscillation circuit in the first embodiment. As shown in FIG. 2, the oscillation circuit 110 includes a resistance element 111, inverters 112 and 113, load capacitances 114 and 115, a variable capacitance diode 116, and a controlled potential regulating circuit 119. This configuration is a so-called Colpitts oscillation circuit, but includes the variable capacitance diode 116 as part of the load capacitance to make it possible to regulate the frequency of the oscillation signal generated in the oscillation circuit.

The resistance element 111 is placed so as to be connected between two terminals of the quartz crystal resonator 100. The inverter 112 is placed so as to be connected between the two terminals of the quartz crystal resonator 100 in parallel with the resistance element 111. The inverter 113 is placed so that an input terminal thereof is connected to an output terminal of the inverter 112, and has an output terminal from which the oscillation signal 118 is output. The load capacitance 114 is placed so as to be connected between one terminal of the quartz crystal resonator 100 and a grounding potential terminal. The load capacitance 115 is placed and connected between the other terminal of the quartz crystal resonator 100 and the variable capacitance diode 116. The variable capacitance diode 116 is placed and connected between one terminal of the load capacitance 115 and the grounding potential terminal. The controlled potential regulating circuit 119 is placed and connected between the load capacitance 115 and the variable capacitance diode 116.

Here, the variable capacitance diode 116 is an element whose capacitance changes according to the voltage applied to the ends thereof. In the first embodiment, the potential applied to the grounding potential terminal is a constant grounding potential, and a controlled potential 117 is a controllable potential. Therefore, by changing the controlled potential 117, the capacitance of the variable capacitance diode 116 changes. When the capacitance of the variable capacitance diode 116 changes, a parameter of the capacitance forming the oscillation circuit 110 changes, and the frequency of the oscillation signal 118 output from the oscillation circuit 110 changes. That is, in the frequency measuring device of the first embodiment, the variable capacitance diode 116 and the controlled potential regulating circuit 119 function as a frequency regulator which can regulate the frequency of the oscillation signal output from the oscillation circuit 110.

The controlled potential regulating circuit 119 generates the controlled potential 117 based on the control signal 140 which is an input signal, and outputs the controlled potential 117 thus generated.

(3) Configuration Example of Controlled Potential Regulating Circuit

Figure 3:
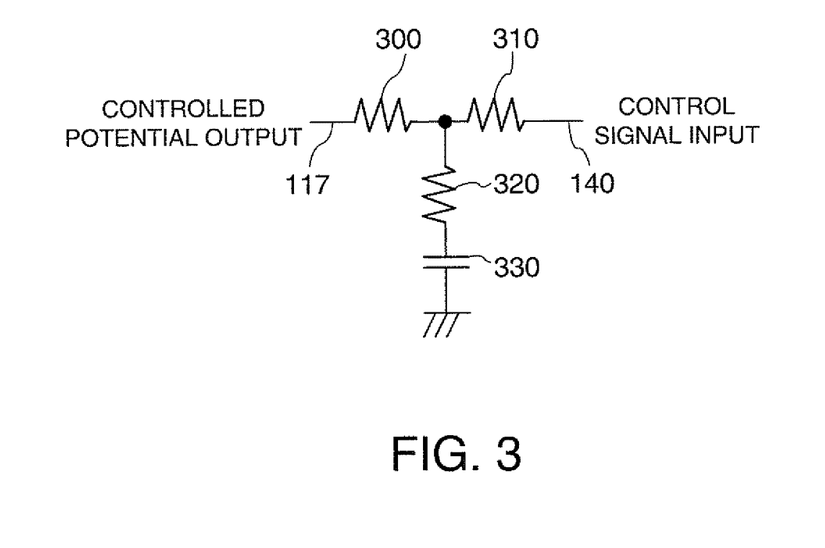
FIG. 3 is a diagram showing a configuration example of a controlled potential regulating circuit.

FIG. 3 is a diagram showing a specific configuration example of the controlled potential regulating circuit 119. As shown in FIG. 3, the controlled potential regulating circuit 119 includes resistance elements 300, 310, and 320 and a capacitance element 330. The controlled potential regulating circuit 119 generates the controlled potential 117 based on the control signal 140 input from the control circuit 130, and supplies the controlled potential 117 thus generated to the oscillation circuit 110.

The resistance elements 300 and 310 are connected in series between a terminal to which the control signal 140 is input and a terminal from which the controlled potential 117 is output. The resistance element 320 is connected between a terminal between the resistance element 300 and the resistance element 310 and one terminal of the capacitance element 330. The capacitance element 330 is connected between one terminal of the resistance element 320 and the grounding potential terminal.

Figure 4:
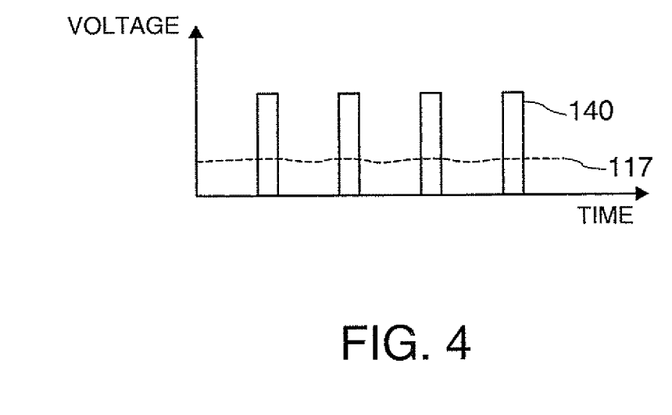
FIG. 4 is a diagram showing an example of the waveform of a control signal.

FIG. 4 is a diagram showing the control signal 140 input to the controlled potential regulating circuit 119 as a voltage change with time. The control signal 140 is a digital signal and changes between two potentials: a predetermined potential and a grounding potential. When the control signal 140 shown in FIG. 4 is input, an analog device forming the controlled potential regulating circuit 119 functions as a low-pass filter, and a predetermined potential appears at the terminal of the controlled potential 117. The controlled potential 117 is determined by the time at which a pulse of the control signal 140 occurs and a pulse width.

(4) Example of Operation of Frequency Measuring Device

Figure 5:
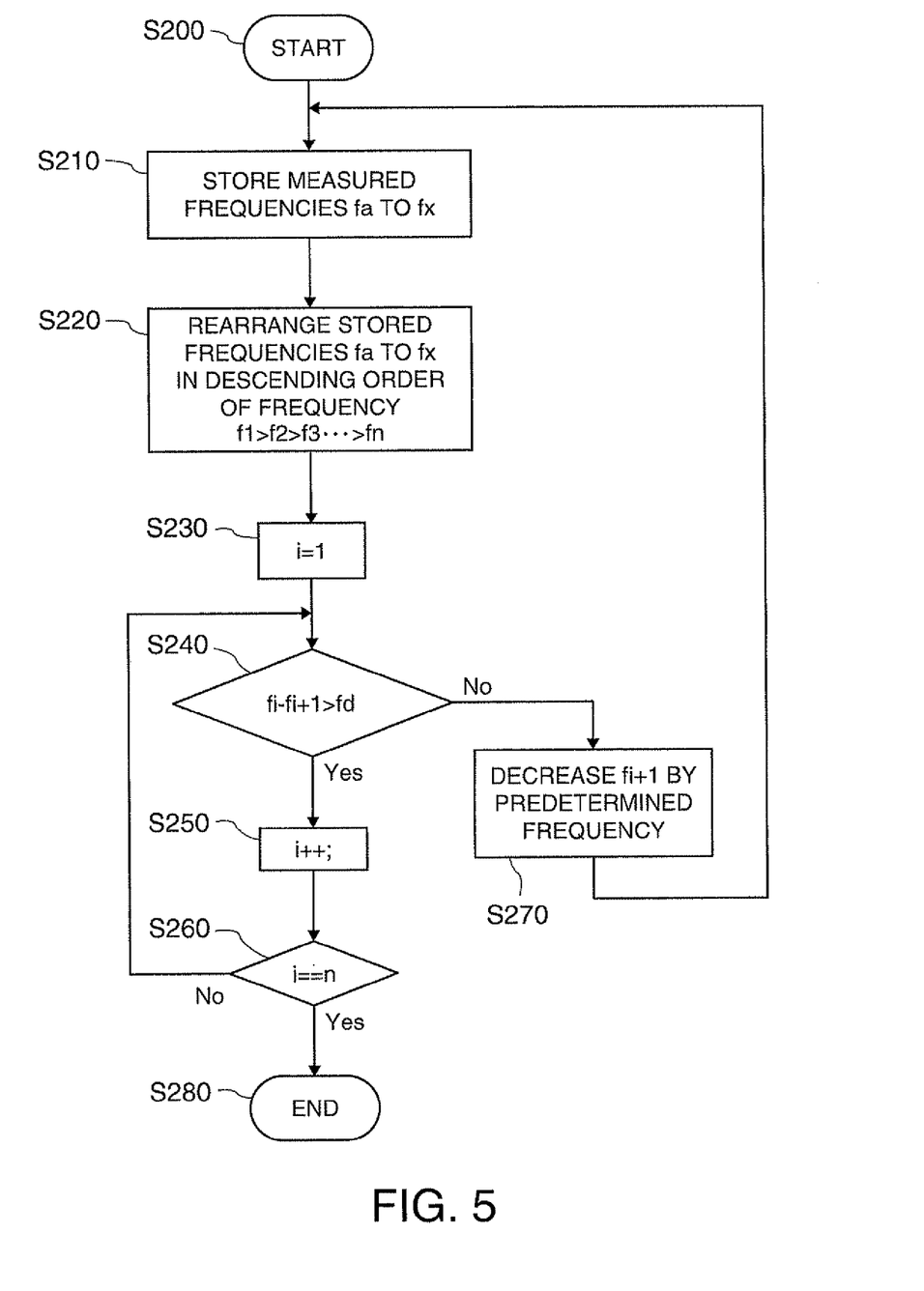
FIG. 5 is a first flowchart explaining the operation of the frequency measuring device.

Here, a specific example of operation regarding a frequency regulating mechanism to prevent the drawing effect of the frequency measuring device will be described with reference to FIG. 5.

When operation of the frequency regulating mechanism to prevent the drawing effect of the frequency measuring device starts (S200), the control circuit 130 stores the frequencies fa to fx of the measured oscillation signals 118a to 118x in a storage area in the control circuit 130 (S210). Next, the control circuit 130 rearranges the stored frequencies fa to fx in descending order of frequency (S220). Here, for convenience of description, symbols f1, f2, f3, . . . fn are assigned to the frequencies in descending order of frequency, and these frequencies are assumed to be f1>f2>f3> . . . >fn. Next, the control circuit 130 performs initialization by setting a variable i at 1 (S230). Then, the control circuit 130 determines whether a difference between the frequency fi and the frequency fi+1 is greater than a predetermined frequency difference fd (for example, 100 Hz) or not (S240). Here, if the difference between the frequency fi and the frequency fi+1 is greater than the predetermined frequency difference fd (Yes), the control circuit 130 adds 1 to the variable i (S250). If the variable i is equal to the number n of oscillation signals 118 (Yes), the control circuit 130 ends the processing (S280). On the other hand, if the variable i is smaller than the number n of oscillation signals 118 (No), the control circuit 130 goes back to S240 and resumes the processing.

Incidentally, when a determination whether or not the difference between the frequency fi and the frequency fi+1 is greater than the predetermined frequency difference fd is made (S240), if the difference between the frequency fi and the frequency fi+1 is smaller than or equal to the predetermined frequency difference fd (No), the control circuit 130 outputs the control signal 140 to the oscillation circuit 110 outputting the oscillation signal 118 corresponding to the frequency fi+1 in order to decrease the frequency f2 by a predetermined frequency (for example, 50 Hz) (S270). Then, the control circuit 130 repeats the processes after S210.

The specific operation of the frequency measuring device has been described as the above flowchart. However, the specific operation of the frequency measuring device can be described as the following concept.

First, the control circuit 130 (a1) specifies a signal having the highest frequency, the signal of the oscillation signals 118a to 118x, as a first signal and specifies a signal having the second highest frequency after the first signal as a second signal based on the frequencies measured by the counter circuits 120a to 120x.

Next, the control circuit 130 (b) compares the first signal and the second signal. When the above comparison reveals that (c1-1) a frequency difference between the frequency f1 of the first signal and the frequency f2 of the second signal is greater than a predetermined frequency difference fd (for example, 100 Hz), the control circuit 130 specifies the second signal as a new first signal until a signal having the lowest frequency, the signal of the oscillation signals 118a to 118x, becomes the second signal, specifies a signal having the second highest frequency after the new first signal as a new second signal, and returns to process (b). On the other hand, (c1-2) when the frequency difference between the first signal and the second signal is smaller than or equal to the predetermined frequency difference fd, the control circuit 130 decreases the frequency of the second signal by controlling the frequency regulator corresponding to any one of the oscillation circuits 110a to 110x, the frequency regulator corresponding to the oscillation circuit outputting the second signal, and returns to process (a1).

By operating as described above, the control circuit 130 can control the frequency regulators so that the frequency difference between the oscillation signals 118a to 118x becomes greater than the predetermined frequency difference.

Incidentally, in the above description, the frequencies of the oscillation signals are regulated so that the frequency difference fd between the oscillation signals 118a to 118x becomes greater than 100 Hz; however, the frequency difference fd is not necessarily limited to 100 Hz. However, it is empirically known that no drawing effect occurs by setting the frequency difference fd at 100 Hz or more. Moreover, it is empirically known that almost no drawing effect occurs by setting the frequency difference fd at 50 Hz or more. Therefore, it can be said that the frequency difference fd between the oscillation signals 118a to 118x is preferably set at 50 Hz or more and more preferably at 100 Hz or more.

Furthermore, in the above description, the control circuit 130 performs a series of processes by rearranging the frequencies fa to fn in descending order of frequency (S220). However, the control circuit 130 may perform a series of processes by rearranging the frequencies fa to fn in ascending order of frequency. In this case, the operation is different from that of the above-described flowchart in that, for example, in S270, the control circuit 130 outputs the control signal 140 to the oscillation circuit 110 outputting the oscillation signal 118 corresponding to the second signal to increase the frequency of the second signal by the predetermined frequency.

Incidentally, the above operation is performed as an adjustment to prevent the drawing effect from occurring during the operation of the frequency measuring device, and is preferably performed with predetermined frequency. For example, when an odor contained in the surrounding medium is detected by using the frequency measuring device, the above operation can be performed as an initial detection adjustment.

Furthermore, it is preferable that the adjustment be made at specified time intervals. However, the adjustment becomes difficult if the frequency of the oscillation signal changes during the adjustment due to a change in the surrounding medium. Therefore, it is preferable to take measures so that the surrounding medium does not change during the adjustment.

Moreover, in order to indicate that the frequency measuring device is being adjusted, a display section or a sound producing section may be provided to inform the user that the frequency measuring device is being adjusted. This allows the user to recognize that the frequency measuring device is being adjusted. More preferably, a valve is provided in a flow channel through which a medium is sent to the area around the quartz crystal resonator included in the frequency measuring device. Furthermore, a mechanism for sending a stable medium such as non-odorous air to the area around the quartz crystal resonator may be provided.

(5) Feature of First Embodiment

According to the frequency measuring device configured as described above, since a frequency difference between the oscillation signals 118a to 118x output from the oscillation circuits 110a to 110x, respectively, are made greater than a predetermined frequency difference, it is possible to prevent the drawing effect from occurring between the oscillation circuits 110a to 110x. This eventually makes it possible to prevent the drawing effect from causing a problem in the operation of the frequency measuring device.

Moreover, when the control circuit 130 performs a series of processes by rearranging the frequencies fa to fn in descending order of frequency (S220), the control circuit 130 performs a process to decrease the frequency when regulating the frequencies of the oscillation signals 118a to 118x. By doing so, it is possible to regulate the frequencies of the oscillation signals 118a to 118x without increasing the power consumption of the frequency measuring device.

On the other hand, when the control circuit 130 performs a series of processes by rearranging the frequencies fa to fn in ascending order of frequency (S220), the control circuit 130 performs a process to Increase the frequency when regulating the frequencies of the oscillation signals 118a to 118x. Also with this method, it is possible to regulate the frequencies of the oscillation signals 118a to 118x appropriately.

Moreover, by adopting the oscillation circuit described in the first embodiment, it is possible to provide a frequency measuring device provided with the oscillation circuits 110a to 110x having a relatively simple configuration.

In addition, as described in the first embodiment, when the frequency regulator further includes a controlled potential regulating circuit (a voltage regulating circuit) which can change the voltage to be applied to the variable capacitance diode 116, it is possible to provide a frequency measuring device which can easily regulate the frequencies of the oscillation signals 118a to 118x by changing the applied voltage.

Moreover, in the first embodiment, the controlled potential regulating circuit is formed of an analog filter circuit. This makes it possible to provide a frequency measuring device provided with a controlled potential regulating circuit with a simple configuration using an analog device.

3. SECOND EMBODIMENT

Next, a second embodiment of the invention will be described with reference to FIGS. 6 and 7. In the second embodiment, a frequency regulator which is different from that of the first embodiment is provided, and the frequency regulator is formed of a drive voltage generating circuit.

Therefore, in the second embodiment, the variable capacitance diode 116 and the controlled potential regulating circuit 119 provided in the frequency measuring device of the first embodiment do not always have to be provided.

(1) Configuration Example of Drive Voltage Generating Circuit

Figure 6:
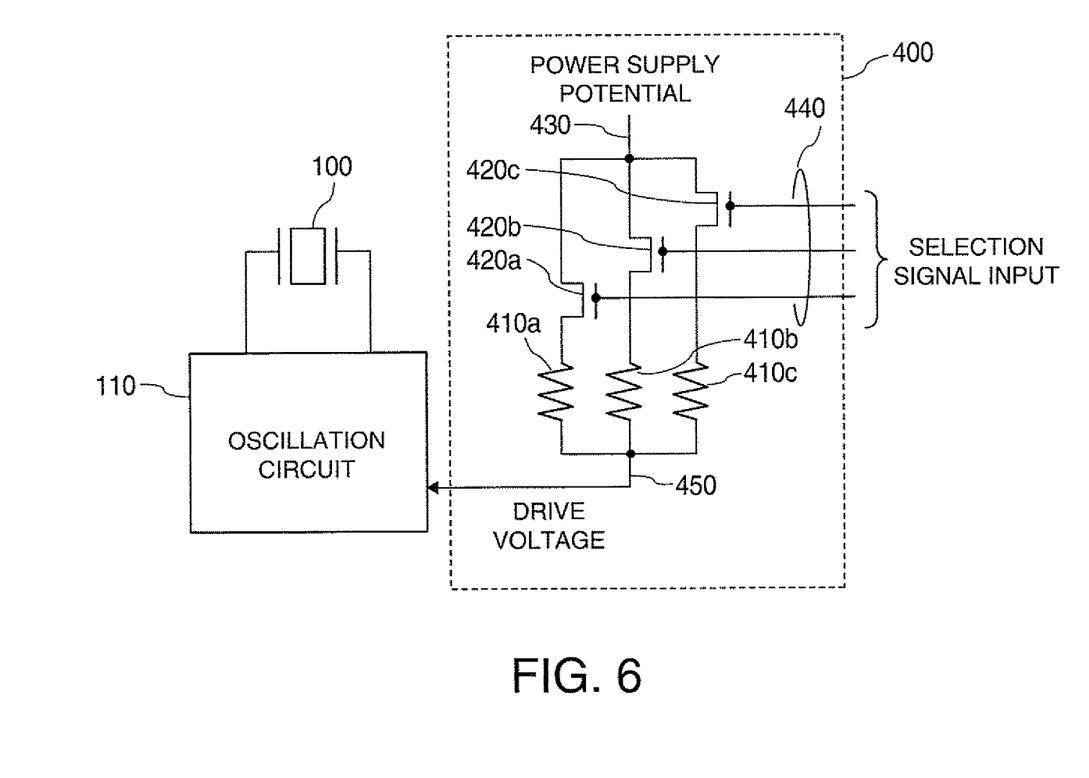
FIG. 6 is a diagram showing a configuration example of a drive voltage generating circuit.

FIG. 6 is a diagram showing a specific configuration of a drive voltage generating circuit 400 functioning as a frequency regulator, an oscillation circuit 110 connected to the drive voltage generating circuit 400, and a quartz crystal resonator 100. The drive voltage generating circuit 400 uses a power supply potential 430 and selection signals 440 as an input, and supplies a drive voltage 450 to the oscillation circuit 110. More specifically, the drive voltage generating circuit 400 includes a plurality of resistance elements 410a to 410c and a plurality of switching elements 420a to 420c. The plurality of resistance elements 410a to 410c and the plurality of switching elements 420a to 420c are configured so that one resistance element and one switching element make one set. The sets formed of the resistance elements 410a to 410c and the switching elements 420a to 420c each have one terminal connected to a power supply potential terminal 430 and the other terminal connected to a drive voltage terminal 450. The selection signals 440 are input to the plurality of switching elements 420a to 420c, and the conducting states of the switching elements 420a to 420c are changed by the selection signals 440.

Here, the plurality of resistance elements 410a to 410c have different resistance values. This configuration makes voltage drops caused by the resistance elements 410a to 410c different, and eventually makes it possible to change the drive voltage 450 by the selection signals 440.

According to the drive voltage generating circuit of the second embodiment, it is possible to change the drive voltage 450 to be applied to the oscillation circuit 110 in the manner described above. When the drive voltage 450 changes, the voltage which drives the inverter 112 forming the oscillation circuit 110 changes. This makes it possible to regulate the frequency of the oscillation signal 118 output from the oscillation circuit 110.

As described above, in the second embodiment, the input signal of the drive voltage generating circuit 400 contains the multi-bit selection signals 440. The selection signals 440 are signals controlled by the control circuit 130; however, if the control circuit 130 outputs the multi-bit selection signals 440, the number of hard wires is increased. Therefore, in the second embodiment, the control signal 140 output from the control circuit 130 is a 1-bit signal, and a serial-parallel converter for generating the multi-bit selection signals 440 based on the control signal 140 is provided.

Figure 7:
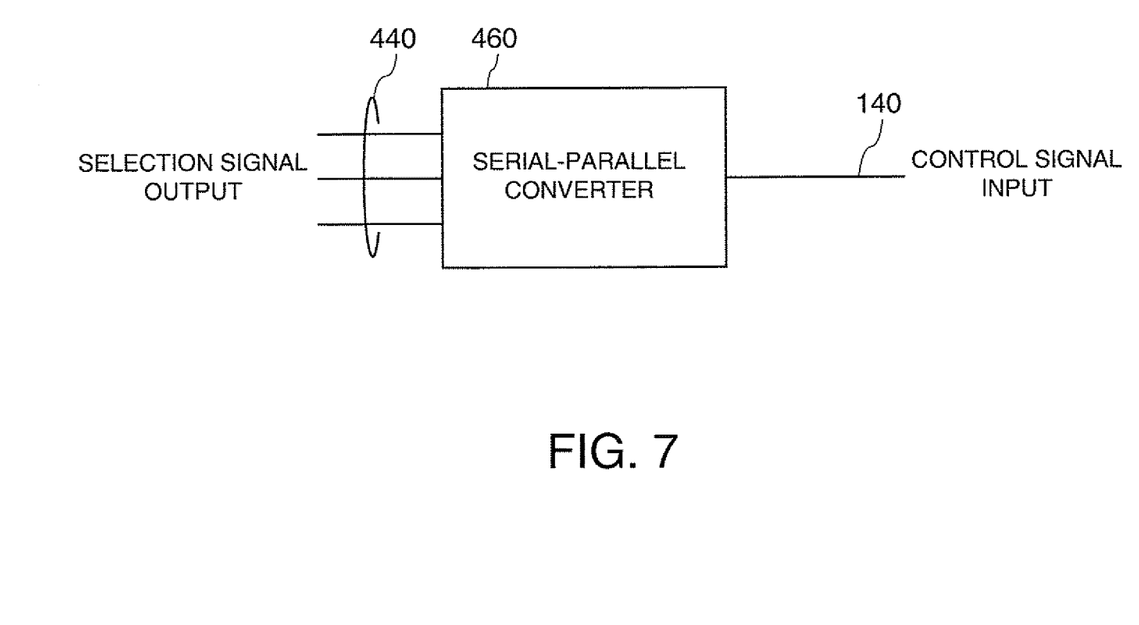
FIG. 7 is a diagram showing a configuration example of a serial-parallel converter.

FIG. 7 is a diagram showing the serial-parallel converter in the second embodiment. As shown in FIG. 7, a serial-parallel converter 460 converts a 1-bit control signal 140 into multi-bit selection signals 440. The serial-parallel converter 460 can be realized by the existing configuration known to a person skilled in the art.

Here, it is preferable that the serial-parallel converter 460 have the function of holding the selection signals 440 to be output. As a result, once the serial-parallel converter 460 receives the control signal 140, the serial-parallel converter 460 can stop the control signal 140 unless it becomes necessary to regulate the oscillation frequency.

Incidentally, the drive voltage generating circuit 400 and the serial-parallel converter 460 are provided in each of the oscillation circuits 110 included in the frequency measuring device, and are part of the configuration of the oscillation circuit 110.

Moreover, the configuration of the drive voltage generating circuit 400 is not limited to the configuration described above. The drive voltage generating circuit 400 can be realized by other configurations such as a step-down circuit, and any configuration devised easily by a person skilled in the art is also included in the invention. However, the above-described configuration is preferable because it can provide a drive voltage generating circuit 400 with a simple configuration.

(2) Feature of Second Embodiment

According to the frequency measuring device configured as described above, the drive voltage generating circuit 400 as the frequency regulator is provided. This makes it possible to provide a frequency measuring device which can regulate the frequencies of the oscillation signals 118 only by changing the drive voltage while allowing the plurality of oscillation circuits 110 of the frequency measuring device to have a commonly-used configuration.

Moreover, as in the second embodiment, by providing the serial-parallel converter 460, it is possible to control the plurality of switching elements 420a to 420c included in the drive voltage generating circuit 400 by a 1-bit control signal 140. This makes it possible to reduce the number of signal lines used and facilitate connection between the control circuit 130 and the oscillation circuit 110, for example.

4. THIRD EMBODIMENT

Figure 8:
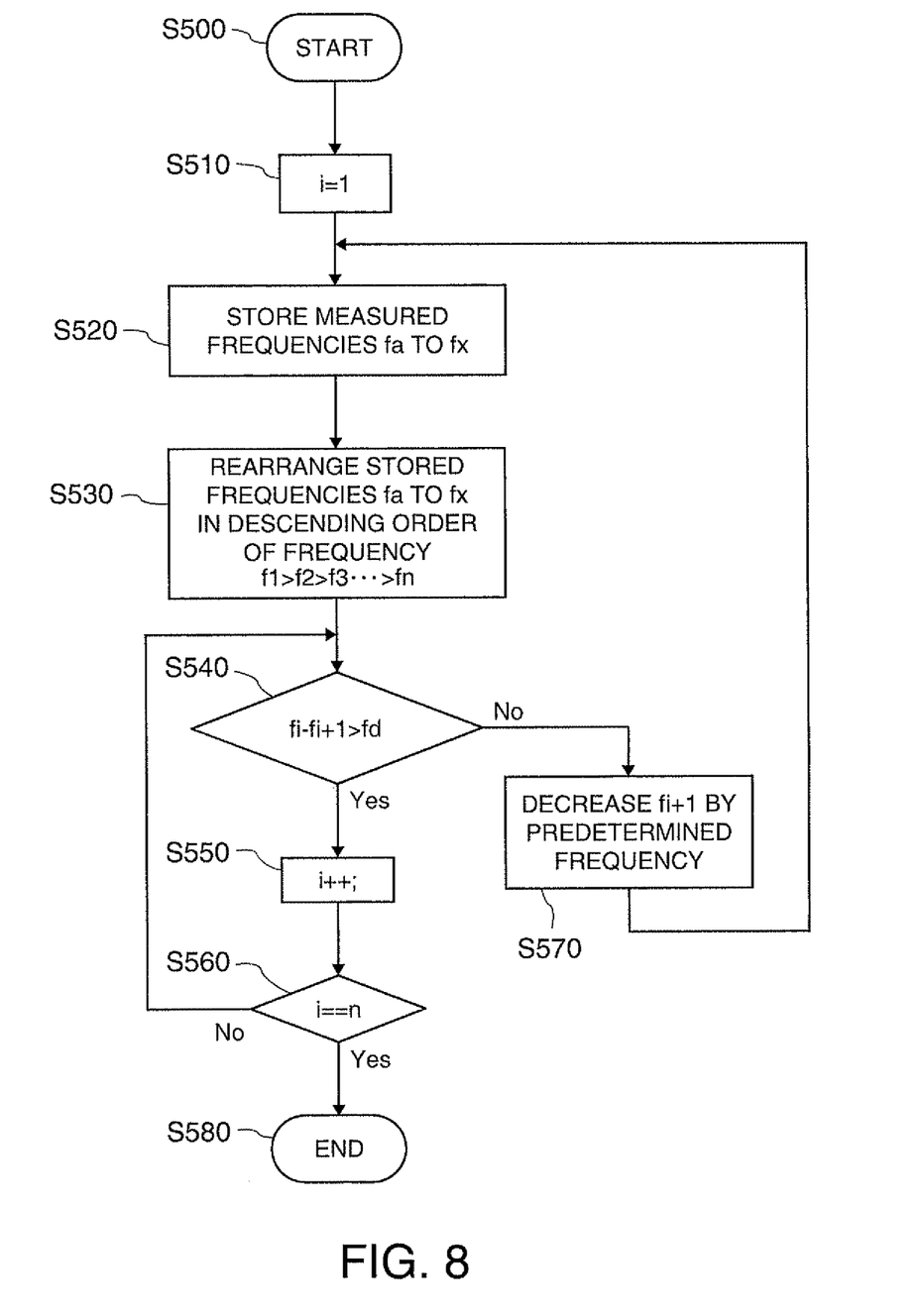
FIG. 8 is a second flowchart explaining the operation of the frequency measuring device.

Next, a third embodiment of the invention will be described with reference to FIG. 8. Although the configuration of a frequency measuring device of the third embodiment is the same as that of the first embodiment, the operation of the frequency measuring device differs from that of the first embodiment. More specifically, in the third embodiment, the time at which a variable i is initialized is changed. As a result, while all the oscillation signals are checked again every time the frequency of any oscillation signal changes in the first embodiment, in the third embodiment, the checked oscillation signal is not checked again, and the next oscillation signal is checked. Hereinafter, the operation of the frequency measuring device in the third embodiment will be described specifically.

(1) Example of Operation of Frequency Measuring Device

When the operation of the frequency, measuring device starts (S500), the control circuit 130 performs initialization by setting a variable i at 1 (S510). Next, the control circuit 130 stores the measured frequencies fa to fx of the oscillation signals 118a to 118x in the storage area in the control circuit 130 (S520). Then, the control circuit 130 rearranges the stored frequencies fa to fx in descending order of frequency (S530). Here, for convenience of description, symbols f1, f2, f3, ... fn are assigned to the frequencies in descending order of frequency, and these frequencies are assumed to be f1>f2>f3> ... >fn. Next, the control circuit 130 determines whether a difference between the frequency fi and the frequency fi+1 is greater than a predetermined frequency difference fd (for example, 100 Hz) or not (S540). Here, if the difference between the frequency fi and the frequency fi+1 is greater than the predetermined frequency difference fd (Yes), the control circuit 130 adds 1 to the variable i (S550). If the variable i is equal to the number n of oscillation signals 118 (Yes), the control circuit 130 ends the processing (S580). On the other hand, if the variable i is smaller than the number n of oscillation signals 118 (No), the control circuit 130 goes back to S540 and resumes the processing.

Incidentally, when a determination whether or not the difference between the frequency fi and the frequency fi+1 is greater than the predetermined frequency difference fd is made (S540), if the difference between the frequency fi and the frequency fi+1 is smaller than or equal to the predetermined frequency difference fd (No), the control circuit 130 outputs the control signal 140 to the oscillation circuit 110 outputting the oscillation signal 118 corresponding to the frequency fi+1 in order to decrease the frequency fi+1 by a predetermined frequency (for example, 50 Hz) (S570). Then, the control circuit 130 repeats the processes after S520.

The specific operation of the frequency measuring device has been described as the above flowchart. However, the specific operation of the frequency measuring device can be described as the following concept.

First, the control circuit 130 (a1) specifies a signal having the highest frequency, the signal of the oscillation signals 113a to 118x, as a first signal and specifies a signal having the second highest frequency after the first signal as a second signal based on the frequencies measured by the counter circuits 120a to 120x.

Next, the control circuit 130 (b) compares the first signal and the second signal. When the above comparison reveals that (c1-1) a frequency difference between the frequency of the first signal and the frequency of the second signal is greater than a predetermined frequency difference fd (for example, 100 Hz), the control circuit 130 specifies the second signal as a new first signal until a signal having the lowest frequency, the signal of the oscillation signals 118a to 118x, becomes the second signal, specifies a signal having the second highest frequency after the new first signal as a new second signal, and returns to process (b). On the other hand, (c3-2) when the frequency difference between the first signal and the second signal is smaller than or equal to the predetermined frequency difference fd, the control circuit 130 decreases the frequency of the second signal by controlling the frequency regulator corresponding to any one of the oscillation circuits 110a to 110x, the frequency regulator corresponding to the oscillation circuit outputting the second signal. Then, the control circuit 130 specifies a signal having the second lowest frequency after the first signal as a new second signal, and returns to process (b).

By operating as described above, as in the first embodiment, the control circuit 130 can control the frequency regulators so that the frequency difference between the oscillation signals 118a to 118x becomes greater than the predetermined frequency difference.

Moreover, in the above description, the control circuit 130 performs a series of processes by rearranging the frequencies fa to fn in descending order of frequency (S530). However, as is the case with the first embodiment, the control circuit 130 may perform a series of processes by rearranging the frequencies fa to fn in ascending order of frequency. In this case, the operation is different from that of the above-described flowchart in that, for example, in S570, the control circuit 130 outputs the control signal 140 to the oscillation circuit 110 outputting the oscillation signal 118 corresponding to the second signal to increase the frequency of the second signal by the predetermined frequency.

(2) Feature of Third Embodiment

According to the operation of the third embodiment, it is possible to control the frequency regulators so that the frequency difference between the oscillation signals 118a to 118x becomes greater than the predetermined frequency difference in a shorter time compared to the operation of the first embodiment.

5. SUPPLEMENT

In addition to a sensor such as an odor sensor, the frequency measuring device described above can be applied to various kinds of electronic equipment.

Incidentally, in the frequency measuring devices described in the embodiments, the counter circuits 120 count the number of changes in the oscillation signals 118 and output the results of counting, and the control circuit 130 derives the frequencies of the oscillation signals 118. However, the configuration is not limited to such a configuration. For example, frequency measuring circuits may be placed in place of the counter circuits 120. In this case, the frequency measuring circuits derive the frequencies of the oscillation signals 118 and output the information on the derived frequencies to the control circuit 130.

Moreover, in the frequency measuring devices described in the embodiments, the control circuit 130 derives the frequencies from the oscillation signals 118. However, the control circuit 130 does not always have to derive the frequency itself, and can use the equivalent of the frequency. For example, the control circuit 130 can regulate the frequencies by obtaining the periods of the oscillation signals 118 with no need to derive the frequencies. That is, the control circuit 130 may measure the frequencies of the oscillation signals 118 indirectly.

Furthermore, in the embodiments, the quartz crystal resonator 100 is used. However, another resonator may be used.

In addition, the embodiments described above can be combined. For example, it is possible to provide a frequency measuring device which includes the frequency regulator of the second embodiment and operates in the manner described in the third embodiment.

What is claimed is:

1. A frequency measuring device, comprising:
a first resonator provided with a first adsorption film;
a second resonator provided with a second adsorption film;
a first oscillation circuit that outputs a first oscillation signal, the first oscillation circuit connecting to the first resonator, the first oscillation circuit being provided with a first frequency regulator, the first frequency regulator regulating a first frequency that is a frequency of the first oscillation signal;
a second oscillation circuit that outputs a second oscillation signal, the second oscillation circuit connecting to the second resonator, the second oscillation circuit being provided with a second frequency regulator, the second frequency regulator regulating a second frequency that is a frequency of the second oscillation signal;
a measuring circuit that measures the first frequency and the second frequency;
a control circuit that controls the first frequency regulator and the second frequency regulator so that a difference between the first frequency and the second frequency becomes greater than a predetermined difference;
a third resonator provided with a third adsorption film;
a third oscillation circuit that output a third oscillation signal, the third oscillation circuit connecting to the third resonator, the third oscillation circuit being provided with a third frequency regulator, the third frequency regulator regulating a third frequency that is a frequency of the third oscillation signal;
the measuring circuit measuring the third frequency,
the control circuit performing:
(a1) specifying a first signal that has the highest frequency of the first frequency, the second frequency, and the third frequency, and specifying a second signal that has the second highest frequency of the first frequency, the second frequency, and the third frequency,
(b) comparing the highest frequency and the second highest frequency, (c1-1) specifying the second signal as a new first signal when a difference between the highest frequency and the second highest frequency is greater than the predetermined difference, specifying a signal having the second highest frequency next to a frequency of the new first signal as a new second signal, and returning to (b), and (c1-2) decreasing a frequency of the second signal by controlling one of the first frequency regulator, the second frequency regulator, and the third frequency regulator when the difference between the highest frequency and the second highest frequency is smaller than or equal to the predetermined difference, and returning to (a1).

2. A frequency measuring device, comprising:

a first resonator provided with a first adsorption film;

a second resonator provided with a second adsorption film;

a first oscillation circuit that outputs a first oscillation signal, the first oscillation circuit connecting to the first resonator, the first oscillation circuit being provided with a first frequency regulator, the first frequency regulator regulating a first frequency that is a frequency of the first oscillation signal;

a second oscillation circuit that outputs a second oscillation signal, the second oscillation circuit connecting to the second resonator, the second oscillation circuit being provided with a second frequency regulator, the second frequency regulator regulating a second frequency that is a frequency of the second oscillation signal;

a measuring circuit that measures the first frequency and the second frequency;

a control circuit that controls the first frequency regulator and the second frequency regulator so that a difference between the first frequency and the second frequency becomes greater than a predetermined difference;

a third resonator provided with a third adsorption film;

a third oscillation circuit that output a third oscillation signal, the third oscillation circuit connecting to the third resonator, the third oscillation circuit being provided with a third frequency regulator, the third frequency regulator regulating a third frequency that is a frequency of the third oscillation signal;

the measuring circuit measuring the third frequency, the control circuit performing:

(a2) specifying a first signal that has the lowest frequency of the first frequency, the second frequency, and the third frequency, and specifying a second signal that has the second lowest frequency of the first frequency, the second frequency, and the third frequency, (b) comparing the lowest frequency and the second lowest frequency, (c2-1) specifying the second signal as a new first signal when a difference between the lowest frequency and the second lowest frequency is greater than the predetermined difference, specifying a signal having the second lowest frequency next to a frequency of the new first signal as a new second signal, and returning to (b), (c2-2) increasing a frequency of the second signal by controlling one of the first frequency regulator, the second frequency regulator, and the third frequency regulator when the difference between the lowest frequency and the second lowest frequency is smaller than or equal to the predetermined difference, and returning to (a2).

3. A frequency measuring device, comprising:

a first resonator provided with a first adsorption film;

a second resonator provided with a second adsorption film;

a first oscillation circuit that outputs a first oscillation signal, the first oscillation circuit connecting to the first resonator, the first oscillation circuit being provided with a first frequency regulator, the first frequency regulator regulating a first frequency that is a frequency of the first oscillation signal;

a second oscillation circuit that outputs a second oscillation signal, the second oscillation circuit connecting to the second resonator, the second oscillation circuit being provided with a second frequency regulator, the second frequency regulator regulating a second frequency that is a frequency of the second oscillation signal;

a measuring circuit that measures the first frequency and the second frequency;

a control circuit that controls the first frequency regulator and the second frequency regulator so that a difference between the first frequency and the second frequency becomes greater than a predetermined difference;

a third resonator provided with a third adsorption film;

a third oscillation circuit that output a third oscillation signal, the third oscillation circuit connecting to the third resonator, the third oscillation circuit being provided with a third frequency regulator, the third frequency regulator regulating a third frequency that is a frequency of the third oscillation signal;

the measuring circuit measuring the third frequency, the control circuit performing:

(a1) specifying a first signal that has the highest frequency of the first frequency, the second frequency, and the third frequency, and specifying a second signal that has the second highest frequency of the first frequency, the second frequency, and the third frequency, (b) comparing the highest frequency and the second highest frequency, (c1-1) specifying the second signal as a new first signal when a difference between the highest frequency and the second highest frequency is greater than the predetermined difference, specifying a signal having the second highest frequency next to a frequency of the new first signal as a new second signal, and returning to (b), (c3-2) decreasing a frequency of the second signal by controlling one of the first frequency regulator, the second frequency regulator, and the third frequency regulator when the difference between the highest frequency and the second highest frequency is smaller than or equal to the predetermined difference, specifying a signal having the second highest frequency next to the highest frequency among the first oscillation signal, the second oscillation signal, and the third oscillation signal as a new second signal, and returning to (b).

4. A frequency measuring device, comprising:

a first resonator provided with a first adsorption film;

a second resonator provided with a second adsorption film;

a first oscillation circuit that outputs a first oscillation signal, the first oscillation circuit connecting to the first resonator, the first oscillation circuit being provided with a first frequency regulator, the first frequency regulator regulating a first frequency that is a frequency of the first oscillation signal;

a second oscillation circuit that outputs a second oscillation signal, the second oscillation circuit connecting to the second resonator, the second oscillation circuit being provided with a second frequency regulator, the second frequency regulator regulating a second frequency that is a frequency of the second oscillation signal;

a measuring circuit that measures the first frequency and the second frequency;

a control circuit that controls the first frequency regulator and the second frequency regulator so that a difference between the first frequency and the second frequency becomes greater than a predetermined difference;
a third resonator provided with a third adsorption film;
a third oscillation circuit that output a third oscillation signal, the third oscillation circuit connecting to the third resonator, the third oscillation circuit being provided with a third frequency regulator, the third frequency regulator regulating a third frequency that is a frequency of the third oscillation signal;
the measuring circuit measuring the third frequency,
the control circuit performing:
(a2) specifying a first signal that has the lowest frequency of the first frequency, the second frequency, and the third frequency, and specifying a second signal that has the second lowest frequency of the first frequency, the second frequency, and the third frequency,
(b) comparing the lowest frequency and the second lowest frequency,
(c2-1) specifying the second signal as a new first signal when a difference between the lowest frequency and the second lowest frequency is greater than the predetermined difference, specifying a signal having the second lowest frequency next to a frequency of the new first signal as a new second signal, and returning to (b),
(c4-2) increasing a frequency of the second signal by controlling one of the first frequency regulator, the second frequency regulator, and the third frequency regulator when the difference between the lowest frequency and the second lowest frequency is smaller than or equal to the predetermined difference, specifying a signal having the second lowest frequency next to the lowest frequency among the first oscillation signal, the second oscillation signal, and the third oscillation signal as a new second signal, and returning to (b).

5. The frequency measuring device according to claim 1,
the control circuit ending a measuring operation when a difference between the first frequency and the second frequency, a difference between the first frequency and the third frequency, and a difference between the second frequency and the third frequency become greater than the predetermined difference.

6. The frequency measuring device according to claim 1,
each of the first oscillation circuit and the second oscillation circuit having:
a resistance element connected between a first terminal and a second terminal,
an inverter connected between the first terminal and the second terminal in parallel with the resistance element,
a variable capacitance element connected between the first terminal and a first potential terminal, and
a first capacitive element connected between the second terminal and the first potential terminal.

7. The frequency measuring device according to claim 6,
each of the first frequency regulator and the second frequency regulator including a voltage regulating circuit that changes a voltage to be applied to the variable capacitance element.

8. The frequency measuring device according to claim 7,
the voltage regulating circuit including an analog filter circuit.

9. The frequency measuring device according to claim 1,
each of the first frequency regulator and the second frequency regulator including a drive voltage regulating circuit that changes a drive voltage.

10. The frequency measuring device according to claim 9, further comprising:
a serial-parallel converter that generates a first selection signal and a second selection signal based on a 1-bit control signal supplied from outside of the serial-parallel converter,
the drive voltage regulating circuit further including:
a first drive voltage regulating resistance element and a first switching element that are connected in series between a terminal that is supplied the drive voltage and a second potential terminal, and
a second drive voltage regulating resistance element and a second switching element that are connected in series between the terminal that is supplied the drive voltage and the second potential terminal, and that are connected in parallel with the first drive voltage regulating resistance element,
a conducting state of the first switching element being changed by the first selection signal and a conducting state of the second element being changed by the second selection signal.

11. An odor sensor provided with the frequency measuring device according to claim 1.

12. An electric equipment provided with the frequency measuring device according to claim 1.

* * * * *